United States Patent [19]

Wristers

[11] 4,025,459
[45] May 24, 1977

[54] NOBLE METAL HYDROGENATION CATALYSTS PROMOTED BY FLUORIDE CONTAINING ACIDS

[75] Inventor: Jos Wristers, Plainfield, N.J.

[73] Assignee: Exxon Research and Engineering Company, Linden, N.J.

[22] Filed: May 14, 1975

[21] Appl. No.: 577,351

[52] U.S. Cl. .................. 252/429 R; 252/433; 252/434; 252/436; 252/439; 252/441; 208/143; 260/667

[51] Int. Cl.² ............... B01J 31/28; B01J 27/12

[58] Field of Search ......... 252/434, 436, 439, 441, 252/429 R, 433

[56] References Cited

UNITED STATES PATENTS

| | | | |
|---|---|---|---|
| 2,406,869 | 9/1946 | Upham | 252/434 |
| 2,425,991 | 8/1947 | Burk et al. | 252/433 X |
| 2,744,148 | 5/1956 | Ruh et al. | 252/441 X |
| 2,848,377 | 8/1958 | Webb | 252/441 X |
| 3,409,684 | 11/1968 | Aristoff | 252/434 X |
| 3,413,362 | 11/1968 | Otaku | 252/436 X |
| 3,497,488 | 2/1970 | Dawans et al. | 252/429 R X |
| 3,590,025 | 6/1971 | Tittle | 252/429 R X |
| 3,799,867 | 3/1974 | Cardwell et al. | 252/441 X |

Primary Examiner—Patrick P. Garvin
Attorney, Agent, or Firm—Joseph J. Allocca

[57] ABSTRACT

Adding liquid HF or liquid Bronsted acids containing fluorine to palladium results in a catalyst which demonstrates enhanced hydrogenation activity on the order of 10 to 144 times that of palladium by itself. Adding a Friedel-Crafts catalyst containing fluorine (e.g. $BF_3$, $TaF_5$) to the liquid HF or liquid Bronsted acids containing fluorine leads to even greater hydrogenation rate increases, e.g. 3500 times. Addition of liquid HF or Friedel-Crafts catalysts containing fluorine in HF or Bronsted acid containing fluorine to platinum also results in a superior catalyst possessing enhanced hydrogenation rates but to a lesser degree than with palladium. However, such liquid acid promoted platinum catalysts are more tolerant to sulfur, than are palladium catalysts, making them attractive as heavy ends, resid and coal liquid hydrogenation catalysts. Iridium has also been discovered to be a good hydrogenation catalyst. When it is used in conjunction with liquid HF, fluorine containing Bronsted acids or Friedel Craft catalysts containing fluorine in liquid HF or Bronsted acid containing fluorine, hydrogenation is increased ~ 150 fold. It is also more tolerant to sulfur than is palladium.

The liquid acid promoted palladium, platinum or iridium catalyst may be supported on a material resistant to acid and not containing any silicon, aluminum or oxygen; carbon, charcoal, teflon etc. meets this requirement.

A process for the hydrogenation of unsaturated hydrocarbon fractions comprises dissolving said unsaturated hydrocarbon fraction in a liquid acid system, said system being selected from the group consisting of liquid HF or Bronsted acid containing fluorine or fluorine-containing Friedel Crafts in liquid HF or Bronsted acid and contacting the resulting solution with the palladium, platinum or iridium catalyst in a pressurized hydrogen atmosphere in the presence of said liquid HF, fluorine containing Bronsted acid or fluoride containing Friedel-Crafts in HF or Bronsted acid system at a temperature sufficient to facilitate the reaction and avoid hydrocracking.

21 Claims, No Drawings

NOBLE METAL HYDROGENATION CATALYSTS PROMOTED BY FLUORIDE CONTAINING ACIDS

DESCRIPTION OF THE INVENTION

Adding liquid HF or liquid Bronsted acids containing fluorine to palladium results in a catalyst demonstrating enhanced hydrogenation activity in the order of 10 to 144 times that of palladium by itself. Adding a Friedel-Crafts catalyst containing fluorine, e.g. boron fluoride, tantalum fluoride, niobium fluoride and mixtures thereof, to the liquid HF or liquid Bronsted acid-containing fluorine leads to even greater hydrogenation rate increases, e.g. 3500 times. Alternatively, addition of liquid HF or a fluoride-containing Friedel-Crafts catalysts in liquid HF or Bronsted acid containing fluorine to platinum also results in enhanced hydrogenation rates but to a lesser degree than with palladium. However, such liquid acid promoted platinum catalysts are more tolerant to sulfur, than are palladium catalysts making them attractive as a heavy ends, resid and coal liquid hydrogenation catalyst. Iridium has also been discovered to be a good hydrogenation catalyst when used in the presence of liquid HF or fluorine containing Bronsted acid or fluorine containing Friedel-Crafts catalysts in liquid HF or Bronsted acid containing fluorine. Hydrogenation is increased approximately 150 fold. Such liquid acid promoted iridium catalysts are more tolerant to sulfur, than are palladium catalysts making them attractive as heavy end, resid and coal liquid hydrogenation catalysts.

The liquid acid promoted palladium, platinum or iridium catalyst may be supported on a material resistant to acid. The support material may be any common material provided it does not contain silicon, aluminum or oxygen. Carbon, charcoal, teflon, etc. meets this requirement.

The palladium may be in the oxide or elemental form, the elemental form being preferred. The platinum and iridium may be in the oxide, sulfide or elemental form, the elemental form being preferred. A process for the hydrogenation of unsaturated hydrocarbon fractions comprises dissolving said unsaturated hydrocarbon fraction in a liquid acid system, said system being selected from the group consisting of liquid HF, Bronsted acid containing fluorine or Friedel-Crafts catalyst containing fluorine in liquid HF or Bronsted acid system and contacting the resulting solution with the supported palladium, platinum or iridium catalyst in a pressurized hydrogen atmosphere in the presence of said liquid acid system at a temperature sufficient to facilitate the reaction and avoid hydrocracking. The unsaturated hydrocarbon fractions comprise aromatic, heterocyclic aromatic, condensed polynuclear aromatic and condensed polynuclear heterocyclic aromatic compounds ranging from $C_6$ to polymeric and the heteroatom is sulfur or nitrogen.

PRIOR ART

The processing of heavy hydrocarbon fractions such as residua, viscous crudes, tars, shale oils and the like is particularly difficult since these fractions contain considerable quantities of both mononuclear and polynuclear aromatic hydrocarbon and heterocyclic aromatic compounds and particularly condensed polynuclear aromatic hydrocarbon compounds and condensed polynuclear heterocyclic aromatic compounds. When these condensed rings compounds are subjected to catalytic cracking, they produce large amounts of coke and gas with only a minor yield of useful liquid product as compared to the yield of liquid product obtained from conventional distillate cracking stocks. Furthermore, these compounds have a high viscosity and in the case of the heterocyclic compounds they have a tendency to form chelate structures with metals. These chelated compounds, when cracked, deposit the metals on the cracking catalyst, which in turn adversely affects the cracking characteristics of the catalyst with respect to product distribution.

A method to circumvent these processing problems has been to hydrogenate the unsaturated compound prior to cracking. It is to be expected that such hydrogenation would result in compounds which can be catalytically cracked more selectively with the production of less coke and a higher yield of useful liquid products. Such hydrogenated products would have lower viscosity and therefore could be more readily handled at lower temperatures and such hydrogenation would reduce the amount of chelated metal present in the cat cracking feedstream thereby avoiding to a great extent catalyst fouling.

Typically, the aromatic hydrocarbons of interest have been reduced at high temperatures, using nickel or other metals as a catalyst in the presence of high hydrogen pressures.

R. Adams and J. R. Marshall in "The Use of Platinum Oxide Platinum Black in the Catalytic Reduction of Aromatic Hydrocarbons", J. Am. Chem. Soc. 50 1970 (1928) revealed the usefulness of noble metal in the catalytic hydrogenation of unsaturated hydrocarbon. Their work was directed to improving the activity of the catalyst. The reaction was carried out with glacial acetic acid as the preferred solvent.

J. H. Broun, H. W. Durand and C. S. Marvel in J. Am. Chem. Soc. 58 (1594) (1936) teach "The Reduction of Aromatic Compounds with Hydrogen and a Platinum Oxide-Platinum Black Catalyst in the Presence of Halogen Acid". The halogen acids used in every experiment were HCl or HBr. It was noted that addition of such acid increased the effectiveness of the platinum oxide-platinum black catalyst.

T. Baker and R. Schuetz in J. Am. Chem. Soc. 69 (1250) 1946 disclosed "High Pressure Hydrogenations with Adams Catalyst". This work extended the usefulness of the original platinum oxide-platinum black catalyst by the expedient of increased hydrogen pressure. All other parameters, such as temperature and solvent (in this case, acetic acid) remained constant.

British Pat. No. 1,104,409 to Shell, teaches an improved process for the "Hydrocracking of Hydrocarbon Oils" which utilizes a tungsten-nickel catalyst on alumina which alumina has a small wt. % of silica and at least 3.5 wt. % fluorine. It must be noted that this invention is directed to a cracking process and not to hydrogenation.

U.S. Pat. No. 3,435,085 to White and Houston, teaches "Aromatic Hydrogenation using a Fluorided Alumina Catalyst". This process hydrogenates aromatics in the presence of sulfur over a nonsiliceous catalyst containing a Group VIII hydrogenation metal disposed on an essentially nonsiliceous support comprising alumina and 10–35% fluorine measured as the element. Platinum is the preferred metal. The patent teaches a reaction run at 650°–900° F. (340°–480° C.) at a pressure above 500 psia, preferably 1000–4000 psia. The support taught is alumina, the fluorine being added to the catalyst before or after deposition of the metal. The addition of fluorine causes a stoichiometric conversion of alumina to aluminum fluoride, that is, the fluorine reacts with the support. Furthermore, the reaction is run without the addition of excess HF. Gaseous or liquid HF or fluorine compounds are used only to initially activate and periodically reactivate the alumina supported catalysts unlike the instant invention which utilizes liquid HF or Bronsted acid containing fluorine or liquid Friedel-Crafts metal fluoride in HF or Bronsted acid containing fluorine system as an actual reactive phase of the process.

U.S. Pat. No. 3,409,684 to Aristoff et al teaches a process for the partial hydrogenation of aromatic compounds which consists of contacting the compound with hydrogen at elevated temperatures and pressures in the presence of a catalyst consisting of a metal hydrogenation component and a Friedel-Crafts metal halide gaseous hydrogen halide component. This patent teaches the necessity of there being a mixture of Friedel-Crafts metal halide and hydrogen halide in combination with the catalytic metal if appreciable hydrogenation rates and yields are to be obtained. The patent, however, utilizes gaseous hydrogen and Friedel-Crafts metal catalyst. The patent broadly discloses palladium on activated carbon with Friedel-Crafts metal halide and gaseous hydrogen halide in the body of the specification and then proceeds by Table IV to demonstrate that such a system, when the halogen is fluorine, is inefficient and undesirable; that to get any appreciable reaction, it is necessary to use both Friedel-Crafts type metal halide and hydrogen halide in combination with the catalytic metal, and in order for there to be a reasonable degree of hydrogenation, temperatures over 100° and pressures exceeding 500 psi and up to 2000 psi are required. This patent in its enumeration of Friedel-Crafts metal halide also does not disclose tantalum pentafluoride or Ir/c. The claims of the case are directed only to aluminum chloride-hydrogen chloride catalyst systems.

The instant invention teaches the unexpected discovery that the addition of liquid HF, Bronsted acid containing fluorine or Friedel-Crafts type metal fluoride catalyst (e.g. boron fluoride, tantalum fluoride, niobium fluoride and mixtures thereof) in liquid HF or Bronsted acid containing fluorine to palladium, produces a catalyst which demonstrates enhanced hydrogenation activity on the order of 14 to 3600 times that of the palladium by itself and this activity enhancement is achieved at low temperature and moderate hydrogen pressures, the temperature ranging from 20° to 200° C., preferably 25°-60° C., most preferably 30° C. Hydrogen pressures on the order of 25 to 5000 psig, preferably 50–1000 psig and most preferably, 100–500 psig, were found to work satisfactorily. The palladium may be deposited on a nonacidic acid resistant support material such as carbon, charcoal, teflon, etc. The support material may be any typical material provided it does not contain silicon, aluminum or oxygen. Reaction times can be from 1 minute to 12 hours, preferably 1 minute to 5 hours, most preferably, 1 minute to 1 hour depending on feed composition and chosen reaction temperature and pressure.

The liquid Bronsted acids containing fluorine may be selected from the group comprising HF, fluorosulfonic acid, trifluoromethane sulfonic acid. The preferred acid is hydrogen fluoride.

The materials which are envisioned as suitable feeds for use with the instant catalyst to yield hydrogenation product comprises unsaturated hydrocarbon fractions, which fractions are aromatic, condensed polynuclear aromatic and condensed polynuclear heterocyclic aromatics ranging from $C_6$ to polymeric typically $C_6$ to $C_{800}$ unsaturated materials and wherein the hetero atoms are sulfur and nitrogen.

It has also been discovered that addition of the Friedel-Crafts metal catalyst $TaF_5$, substantially enhances the rate of reaction selectivity to desired products and yields at temperatures up to 50° C. and hydrogen pressures of 400 psig. Temperatures above 50° C. are to be avoided as above 50° C hydrocracking occurs with $TaF_5$ seriously interfering with the desired hydrogenation. Preferably, the reaction temperature is 30° C.

With other fluoride containing Friedel-Crafts catalysts in hydrogen fluoride, it has been discovered that the prior art teaching of the necessity of there being high temperatures and/or high hydrogen pressures is applicable only to gaseous acid systems, a rate increase by contrast of over 3600 being observed with liquid systems at 30° C and 400 psig (see Run 4, Table I) in the instant invention.

Addition of liquid HF or acids containing HF to platinum or iridium also produces a catalyst with improved hydrogenation activity and superior sulfur resistance. These catalytic materials in elemental, oxide or sulfide form may be supported on a nonacidic acid resistant support material, any typical material being satisfactory, provided it does not contain silicon, aluminum or oxygen; carbon, charcoal, teflon etc. are satisfactory. The support of choice is carbon.

The catalysts of this invention comprise 0.01 to 10% Pd, Pt or Ir, preferably 1–7%, most preferably, 5% Pd, Pt or Ir. The palladium may be in oxide or elemental metal form, elemental metal being preferred, while the Pt or Ir may be in elemental oxide or sulfide form. These catalyst materials may be supported on a nonacidic acid resistant carrier, such as carbon, charcoal, teflon, etc. This catalyst is then promoted with a liquid acid system selected from the group consisting of liquid HF acid, Bronsted acid containing fluorine or Friedel-Crafts metal fluoride in liquid HF or Bronsted acid containing fluorine. The reaction is run in the presence of the liquid acid system as a reaction media component.

Catalysts of the above composition demonstrate synergistic rate, yield and selectivity enhancements as compared to metal catalysts or acid catalysts alone and produce the superior result at lower temperatures and pressures than the prior art, temperatures of choice being between 20°–200° C., preferably 25°–60° C, most preferably, 30° C. Hydrogen pressures range from 25–5000 psig, preferably 50–1000 psig, most preferably 100–500 psig.

The following examples will demonstrate the superiority of the instant invention but are not to be construed as limitations on the scope or breadth of the invention, various modifications being within the ability of those skilled in the art and clearly within the realm of the invention.

The amount of Friedel-Crafts metal fluoride which is added to the liquid HF or Bronsted acid containing fluorine is entirely within the discretion of the practitioner, a ratio of from 1:1000 to 1:1 Friedel-Crafts metal fluoride:Bronsted acid containing fluorine being entirely consistent with the object and operability of the instant invention.

The instant invention also constitutes a process for hydrogenating homocyclic and heterocyclic, mononuclear and polynuclear aromatic compounds which utilizes the catalyst revealed above. When these aromatic compounds dissolved in alkane solvents are brought in contact with the catalyst of the instant invention, the aromatic compound is abstracted into the liquid acid phase. The saturated paraffin solvent is insoluble in the liquid acid phase. The aromatic compound dissolved in the acid is protonated to the carbonium ion species and this species contacts the metal catalyst, at which time the aromatic material became hydrogenated and being insoluble with acid, migrates to the paraffin phase. Additional aromatic material in the paraffin solvent can, consequently, dissolve in the acid phase thereby constituting a continuous separation.

EXAMPLE 1

A number of experiments were run to determine the effect of using different acids in conjunction with different noble metals as catalysts for the hydrogenation 0.100 moles of mesitylene, Table I.

The experimental procedure followed is described for run number 5. A similar procedure was followed for all the runs described in this example and the following examples. To a 300 cc Hasteloy-C autoclave was added 1.0 g 5% Pd/C, 12.0g (0.100 mole) mesitylene, 55.2 g (0.200 mole) tantalum pentafluoride, and 46.0 g (2.3 moles) of hydrogen fluoride. The autoclave was stirred, heated to 30° C, and pressured with 400 psig hydrogen. As hydrogen was consumed the pressure dropped. When the pressure dropped to 360 psig, hydrogen was added to bring the pressure back to 400 psig. When hydrogen consumption ceased, the total product was added to ice, heated to room temperature and extracted with ether. The combined ether extracts were washed with aqueous sodium bicarbonate, and then water. They were dried and the solvent was removed at reduced pressure. The yield was 8.4 g. 70%. The product was then analyzed by a combination of mass spectroscopy, nuclear magnetic resonance and gas chromatography. This analysis indicated that approximately 94% of the material was trimethylcyclohexane or isomers thereof. The other 6% product was mesitylene that had been clogged in a dipleg and thus never come in contact wwith the catalyst.

On the basis of the product analysis and the hydrogen consumption one could calculate when one half of the mesitylene was hydrogenated. This point was designated t½. This t½ was divided into the t½ that was obtained for the similar reaction run at the same temperature but in the absence of any acid. This produced the rate increase for run 5 is obtained by dividing the t½ of run 2 by that of run 5; the rate increase of run 7 is obtained by dividing the t½ of run 1 by that of run 7; and the rate increase of run 9 is obtained by dividing the t½ of run 8 by that of run 9.

TABLE I

| Run | Acid, moles | Metal 5 %/C. g | Temp. ° C | t½ Minutes | Rate Increase t½No Acid ÷ t½Acid Catalyzed |
|---|---|---|---|---|---|
| 1* | None | Pd/C, 1.0 | 50 | 5,458 | — |
| 2* | None | Pd/C, 1.0 | 30 | 12,717** | — |
| 3 | HF, 2.2 | Pd/C, 1.0 | 30 | 88 | 144 |
| 4 | HF/BF₃, 2.3/0.23 | Pd/C, 1.0 | 30 | 3.5 | 3630 |
| 5 | HF/TaF₅, 2.3/0.20 | Pd/C, 1.0 | 30 | 5.0 | 2540 |
| 6 | TaF₅, 0.20 | Pd/C, 1.0 | 30 | — | 0 |
| 7* | HF, 0.075 | Pd/C, 1.0 | 50 | 90 | 61 |
| 8* | None | Ir/C, 1.8 | 30 | 1,300 | — |
| 9 | HF/TaF₅, 2.2/0.20 | Ir/C, 1.8 | 30 | 8.5 | 153 |
| 10* | None | Pt/C, 1.83 | 30 | 299 | — |
| 11 | HF/TaF₅, 2.4/0.20 | Pt/C, 1.83 | 30 | 22 | 14 |
| 12 | None | Ru/C, 5.0 | 30 | 8.5 | — |
| 13 | HF/TaF₅, 2.36/0.20 | Ru/C, 5.0 | 30 | 17,372 | 0.0005 |
| 14 | None | Rh/C, 5.10 | 37 | 2.3 | — |
| 15 | HF/TaF₅, 2.21/0.20 | Rh/C, 5.10 | 30 | 26 | 0.09 |
| 16 | HCl, 1.38, 1.38 | Pd/C, 1.0 | 30 | — | 0 |
| 17 | HCl/AlCl₃, 1.03/0.10 | Pd/C, 1.0 | 30 | — | 0 |
| 18 | HBr/AlBr₃, 0.97/0.10 | Pd/C, 1.0 | 30 | — | 0 |
| 19 | HCl, 1.09 | Pt/C, 1.0 | 30 | 84 | 3.6 |
| 20 | HCl/AlCl₃, 0.92/0.100 | Pt/C, 1.0 | 30 | 324 | 0.92 |

* Used 103 ml of pentane as the solvent.
** estimated

These runs demonstrate the following:

Run 3 demonstrates that liquid HF catalyzes the hydrogenation ability of palladium on carbon.

Runs 4 and 5 demonstrate that adding a Friedel-Crafts catalyst to liquid HF increases the hydrogenation ability of the acid even more.

Run 6 demonstrates that a Friedel-Crafts alone does not catalyze the hydrogenation of palladium on carbon.

Run 7 demonstrates that only gaseous amounts of HF need to be present in order for rate enhancements to be observed.

Runs 9 and 11 demonstrate that HF acids catalyze the hydrogenation ability of iridium on carbon and also of platinum on carbon.

Runs 13 and 15 demonstrate that HF acids do not catalyze the hydrogenation ability of noble metals besides Pd, Pt and Ir. In fact they inhibit the hydrogenation ability of Ru and Rh.

Runs 16, 17 and 18 demonstrate that acids other than ones containing HF do not catalyze the hydrogenation ability of palladium. In fact HCl, HCl/AlCl₃ and HBr/AlBr₃ completely deactivate the hydrogenation ability of Pd/C.

Runs 19 and 20 demonstrate that acids other than ones containing HF do not have much effect on the hydrogenation ability of platinum. Analyses of the products on run 19 indicated that some products were formed that were not formed in any of the other experiments. These products were either isomers of completely hydrogenated mesitylene or chlorinated trimethylcyclohexane.

EXAMPLE 2

A number of experiments were run to establish that the HF catalyzed palladium on carbon hydrogenation was a general reaction in terms of aromatic feeds. In each run 0.10 mole of the aromatic, the acid, and 5% palladium on carbon were charged. All reactions were run at 30° C. In runs 24 through 27, 103 ml of pentane was used as a solvent. The experimental procedure, hydrogen pressure, and work-up was the same as in Example 1.

TABLE II

| Run | Aromatic | Acid, Moles | $t_{1/2}$ Minutes | Rate Increase $t_{1/2}$ No Acid ÷ $t_{1/2}$ Acid Catalyzed |
|---|---|---|---|---|
| 21* |  | — | 4,500 | — |
| 22 |  | HF, 2.4 | 182 | 25 |
| 23 |  | HF/TaF$_5$, 2.4/0.20 | 26 | 173 |
| 24 |  | — | 3,251 | — |
| 25 |  | HF, 0.045 | 185 | 18 |
| 26 | 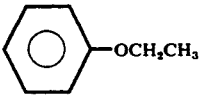—OCH$_2$CH$_3$ | — | 1,620 | — |
| 27 | 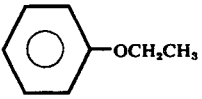—OCH$_2$CH$_3$ | HF, 0.05 | 175 | 9 |

*Used 1.0 mole of benzene. The $t_{1/2}$ was based on hydrogenating 0.05 moles of the benzene.

Runs 21 through 27 demonstrate that adding HF acids to palladium increases its hydrogenation activity. The acid can be liquid HF (run 22), liquid HF/TaF$_5$ (run 23), or gaseous HF (run 25 or 27). The acid can also contain functional groups such as oxygen (run 27).

EXAMPLE 3

One experiment was run to demonstrate the applicability of using an HF promoted palladium on carbon catalyst to hydrogenate a $C_{14}$–$C_{17}$ commercial solvent distillate. The $C_{14}$–$C_{17}$ paraffinic solvent contains about 5% aromatics. The saleable solvent must have less than 1% aromatic. This level is accomplished by hydrogenating the aromatics. Two experiments were run in a 300 cc Hasteloy-C autoclave. One utilized an HF-Pd/C hydrogenating catalyst and the other only Pd/C. Both utilized 100 ml of distillate and were run at 150° C. The initial hydrogen pressure was 350 psig. The rate and the quantity of hydrogen that was consumed was used to measure the progress of the reaction. The reaction was run until no further hydrogen was consumed.

TABLE III

| Run | Acid Moles | Total Hydrogen Consumption PSIG | $t_{1/2}$, time to reach One-Half of H$_2$ Consumption Minutes | Rate Increase $t_{1/2}$ run 28 ÷ $t_{1/2}$ run No. 29 |
|---|---|---|---|---|
| 28 | | 137 | 50 | |
| 29 | HF, 0.18 | 159 | 20 | 2.5 |

Run 29 demonstrates that adding HF to Pd/C leads to a 250% rate increase in hydrogenating $C_{14}$–$C_{17}$ distillate. The resultant product contains less then 0.5% aromatics and thus surpasses the required product specifications. The total hydrogen consumption in the HF-Pd/C reaction is also greater than in the Pd/C, reaction (159 vs 139 psig H$_2$) thus indicating that the extent of hydrogenation in the acid catalyzed reaction is more complete.

EXAMPLE 4

A number of experiments were carried out to differentiate the liquid acid-Pd/C hydrogenation catalyst from the gaseous acid-Pd/C hydrogenations disclosed in U.S. Pat. No. 3,409,684. Anthracene was used in these studies. The results obtained with anthracene are analogous to the results obtained in model systems involving pyrene. All the equipment, procedure and work-up are the same as described in the previous example. Table IV presents the results.

TABLE IV

| Experiment | 30<br>4293-32 | 31<br>3540-20 | 32<br>4026-129 | 33<br>2907-69 |
|---|---|---|---|---|
| HF, mole | — | 0.20 | 2.3 | 2.3 |
| TaF$_5$, mole | — | — | 0.20 | 0.20 |
| Pd/C 5%, g. | 1.0 | 1.0 | 1.0 | — |
| Pentane, mole | 0.9 | 0.9 | — | — |
| Hydrogen Press. Range, psig | 1000 | 900–1000 | 400–500 | 810–815 |
| Temperature, ° C. | 100 | 100 | 70 | 80 |
| Time, hrs. | 4 | 3 | 6.5 | 19.5 |
| Hydrogen Press. Consumption, psig. | 70 | 310 | 1464 | 0 |
| Products and Recovered | | | | |
| Anthracene | | | | |
|   Anthracene | 32% | 0% | traces | 100% |
|   Partially hydrogenated Anthracene | 68% | 100% | 0% | 0% |
|   Completely hydrogenated Anthracene | 0% | traces | 27% | 0% |
|   Hydrocracked Products | 0% | 0% | 73% | 0% |

Run 30 indicates that in the absence of any acid Pd/C has little hydrogenation ability at these mild conditions only 70 psig of hydrogen is consumed and no completely hydrogenated anthracenes are formed.

Run 31 indicates that the addition of small amounts of HF catalyzes the hydrogenation activity of Pd/C. 310 psig of hydrogen were consumed as opposed to almost no hydrogen in the preceding run done in the absence of any acid. Only partially hydrogenated anthracenes, but no completely hydrogenated anthracenes were formed.

Run 32 indicates that liquid HF/TaF$_5$ catalyzes the hydrogen of Pd/C much more so than gaseous HF. The hydrogen uptake is 1464 psig as opposed to 310 psig in the gaseous HF experiment. Note also that the temperature is 30° C. less than in the liquid acid experiment so one would expect much less hydrogen consumption. Only completely hydrogenated anthracenes are formed in this system. Some of these completely hydrogenated antracenes are hydrocracked by the acid at these high temperatures. However, at lower temperatures they can all be easily separated with minimal hydrocracking.

Run 33 indicates that in the absence of Pd/C, liquid HF/TaF$_5$ has no hydrogenating ability.

What is claimed is:

1. A hydrogenation catalyst comprising a liquid acid system promoted material, said liquid acid system being selected from the group consisting of liquid fluorine containing Bronsted acid and fluorine containing Friedel-Crafts catalyst in liquid fluorine containing Bronsted acid and said liquid acid promoted material being selected from the group consisting of the elemental, oxide and sulfide forms of platinum and iridium and the elemental and oxide forms of palladium.

2. The catalyst of claim wherein the liquid fluorine-containing Bronsted acid is selected from the group consisting of liquid HF, fluorosulfonic acid and trifluoromethane sulfonic acid.

3. The catalyst of claim 1 wherein the acid system is a fluorine containing Friedel-Crafts catalyst in liquid HF or fluorine containing Bronsted acid.

4. The catalyst of claim 3 wherein the fluorine-containing Friedel-Crafts catalyst is selected from the group consisting of boron fluoride, tantalum fluoride and niobium fluoride.

5. The catalyst of claim 4 wherein the fluorine-containing Friedel-Crafts catalyst is BF$_3$.

6. The catalyst of claim 5 wherein the BF$_3$ is in liquid HF.

7. A catalyst for the hydrogenation of heavy feeds containing sulfur which catalyst is selected from the group consisting of the elemental, oxide and sulfide forms of platinum and iridium promoted with a liquid acid system, said liquid acid system being selected from the group consisting of liquid fluorine containing Bronsted acid and fluorine containing Friedal-Crafts catalyst in liquid fluorine containing Bronsted acid.

8. The catalyst of claim 7 wherein the fluorine-containing Friedel-Crafts catalyst is selected from the group consisting of boron fluorides, tantalum fluorides and niobium fluorides.

9. The catalyst of claim 8 wherein the Friedel-Crafts catalyst is BF$_3$.

10. The catalyst of claim 9 wherein the platinum and iridium are in the elemental form.

11. The catalyst of claim 7 wherein the catalyst is promoted platinum.

12. The catalyst of claim 7 wherein the catalyst is promoted iridium.

13. The catalyst of claim 7 wherein the liquid fluorine containing Bronsted acid is liquid HF.

14. The hydrogenation catalyst of claim 1 wherein the fluorine containing Friedel-Crafts catalyst in liquid fluorine containing Bronsted acid is present at a ratio of from 1:1000 to 1:1 fluorine containing Friedel-Crafts catalyst to liquid fluorine containing Bronsted acid.

15. The catalyst of claim 7 wherein the fluorine containing Friedel-Crafts catalyst in liquid fluorine containing Bronsted acid is present at a ratio of from 1:1000 to 1:1 fluorine containing Friedel-Crafts catalyst to liquid fluorine containing Bronsted acid.

16. The catalyst of claim 1 wherein said platinum, palladium and iridium are supported on a nonacidic acid resistant support which does not contain any silicon, aluminum or oxygen.

17. The catalyst of claim 16 wherein said nonacidic acid resistant support is selected from the group consisting of carbon, charcoal and polytetrafluoroethylene.

18. The catalyst of claim 7 wherein the platinum or iridium is supported on a nonacidic acid resistant support which does not contain any silicon, aluminum or oxygen.

19. The catalyst of claim 18 wherein the nonacidic acid resistant support is selected from the group consisting of carbon, charcal and polytetrafluoroethylene.

20. The catalyst of claim 17 wherein the non-acidic acid resistant support is carbon.

21. The catalyst of claim 19 wherein the non-acidic acid resistant support is carbon.

* * * * *

UNITED STATES PATENT OFFICE
CERTIFICATE OF CORRECTION

Patent No. 4,025,459            Dated May 24, 1977

Inventor(s) Jos Wristers

It is certified that error appears in the above-identified patent and that said Letters Patent are hereby corrected as shown below:

Column 10, line 68 insert claim:
-- 22. The catalyst of claim 1 wherein the platinum, iridium and palladium are in the elemental form.--

On the cover sheet, after the abstract,

"21 Claims" should read -- 22 Claims --

*Signed and Sealed this*

*Twentieth* Day of *December 1977*

[SEAL]

*Attest:*

RUTH C. MASON
*Attesting Officer*

LUTRELLE F. PARKER
*Acting Commissioner of Patents and Trademarks*